(12) United States Patent
Hamasaki et al.

(10) Patent No.: US 10,959,915 B2
(45) Date of Patent: Mar. 30, 2021

(54) PRODUCTION METHOD FOR EASY-TO-TAKE SOLID PREPARATION, AND EASY-TO-TAKE SOLID PREPARATION

(71) Applicant: DAICEL CORPORATION, Osaka (JP)

(72) Inventors: Momoko Hamasaki, Himeji (JP); Anan Sakaguchi, Himeji (JP); Tomohito Okabayashi, Himeji (JP); Naohiro Hashikawa, Himeji (JP); Takahiro Hiramura, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 15/737,939

(22) PCT Filed: Jun. 28, 2016

(86) PCT No.: PCT/JP2016/069112
§ 371 (c)(1),
(2) Date: Dec. 19, 2017

(87) PCT Pub. No.: WO2017/002796
PCT Pub. Date: Jan. 5, 2017

(65) Prior Publication Data
US 2018/0168934 A1 Jun. 21, 2018

(30) Foreign Application Priority Data
Jun. 29, 2015 (JP) .............................. JP2015-129529

(51) Int. Cl.
*A61J 3/10* (2006.01)
*A61J 3/00* (2006.01)
*A61K 9/28* (2006.01)
*B30B 11/34* (2006.01)
*A61J 3/06* (2006.01)

(52) U.S. Cl.
CPC ................. *A61J 3/10* (2013.01); *A61J 3/005* (2013.01); *A61J 3/06* (2013.01); *A61K 9/286* (2013.01); *A61K 9/2826* (2013.01); *A61K 9/2866* (2013.01); *A61K 9/2893* (2013.01); *B30B 11/34* (2013.01)

(58) Field of Classification Search
CPC ...... A61J 3/10; A61J 3/00; A61K 9/28; B30B 11/34
See application file for complete search history.

(56) References Cited

FOREIGN PATENT DOCUMENTS

| EP | 2 762 167 | 8/2014 |
| JP | H09104621 | 4/1997 |
| JP | 2013132285 | 7/2013 |
| JP | 2014532704 | 12/2014 |
| WO | 0126632 | 4/2001 |

OTHER PUBLICATIONS

International Search Report of International Application No. PCT/JP2016/069112 dated Aug. 23, 2016.
Bajpai, M. et al., "Design and In Vitro Evaluation of Compression-coated Pulsatile Release Tablets of Losartan Potassium", Indian Journal of Pharmaceutical Sciences, 2012, vol. 74(2), pp. 101-106.
Jahn, T. et al., "Press Chamber Coating as External Lubrication for High Speed Rotary Presses: Lubricant Spray Rate Optimization", Drug Development and Industrial Pharmacy, 2005, vol. 31(10), pp. 951-957.
Supplementary European Search Report of Application No. 16817904.2 dated Jan. 24, 2019.

*Primary Examiner* — Zohreh A Fay
(74) *Attorney, Agent, or Firm* — Ping Wang; Morris, Manning & Martin LLP

(57) ABSTRACT

The purpose of present invention to provide a method for the production of an easy-to-take solid preparation, which is mainly characterized in that a coating processing for the easy-to-take property is simply performed by using a gelling agent in a dry process, without going through a wet condition, the easy-to-take solid preparation and the like.
The present invention relates to a dry-process method for the production of an easy-to-take solid preparation wherein a compression-molded core is coated with a coating agent comprising a gelling agent that will show slipperiness when it is brought into contact with water, comprising directly applying only powder of the coating agent to a mortar inner surface, the bottom end surface of an upper-pestle, and the top end surface of a lower-pestle, and subsequently loading and integrally compression-molding a core-molding material; a powder composition for coating the solid preparation, which comprises a water-soluble polymer to be used in the aforementioned production method, and the like.

8 Claims, No Drawings

PRODUCTION METHOD FOR EASY-TO-TAKE SOLID PREPARATION, AND EASY-TO-TAKE SOLID PREPARATION

TECHNICAL FIELD

The present invention relates to a method for the production of an easy-to-take solid preparation, which is mainly characterized in that a coating processing for providing an easy-to-take property is simply performed in a dry process, to the easy-to-take solid preparation and the like.

BACKGROUND ART

Taking properties of a preparation for oral administration have been previously improved for patients who have difficulty in swallowing, and elderly people and children who have a weak swallowing ability and the like.

For example, the preparations are formulated into liquid or jelly preparation form in many cases. However, when a content of a main drug is high, it will be difficult to mask its taste. And, when an active ingredient such as a drug is unstable in water, it will be difficult to be formulated in any preparation form.

Accordingly, easy-to-take preparations have been recently developed for facilitating swallowing of the solid preparation, wherein the surface of the preparations is coated with a gelling agent so that they will show slipperiness and become slippery against mucous membrane and easy to swallow when they are brought into contact with water in oral cavity.

These techniques use processes such as, for example, 1) formulating gel into a tablet by freeze-drying of; 2) punching into a circle shape a film of gelling layers comprising a drug layer between them; 3) punching into a circle shape gelling film layers comprising a tablet between them; 4) spraying a coating solution for gelling on a tablet, and the like.

Patent Literature (PTL) 1 discloses a coating composition for use in an easy-to-take solid preparation, which comprises a first thickener of a metal-crosslinking thickener, a polyvalent metal compound, and a second thickener; a method for the production of a preparation for oral administration by spray-coating alcohol solution having the coating composition dispersed therein onto a drug core comprising an active ingredient; and the preparation for oral administration produced thereby.

Patent Literature (PTL) 2 discloses a powder compression-molding machine to perform simultaneously compression molding of an inner core (core tablet); and a manufacturing method of a product, comprising applying a lubricant to a mortar inner surface, the bottom end surface of an upper-pestle, and the top end surface of a lower-pestle with a first injection device, applying a coating agent over the resulting lubricant layer with a second injection device, filling the mortar with powder, and subsequently compressing the powder with the upper- and lower-pestles.

However, neither of these Patent Literatures discloses or suggests a dry method for the production of an easy-to-take solid preparation that is coated with a gelling agent.

RELATED ARTS

Patent Literatures

PTL 1: International Publication Pamphlet WO2011/125798
PTL 2: JP-A-2012-35289

SUMMARY OF INVENTION

Problems to be Solved by the Invention

The conventional treatment with a gelling agent as seen in the prior arts such as PTL 1 was complicated as it requires the preparation of a gelling agent solution, the transfer to a coating machine after the compression molding and the like. Furthermore, a functional or active ingredient cannot be used if their stability for a solvent in these processes is low.

The mechanism and operation of the plural injection devices of the powder compression-molding machine of PTL 2 is complicated as well.

Accordingly, an object of the present invention is to solve such technical problems in the arts, and to provide a method for the production of an easy-to-take solid preparation, which is mainly characterized in that a coating processing for providing the easy-to-take property is simply performed by using a gelling agent in a dry process, without going through a wet condition, the easy-to-take solid preparation and the like. The term "easy-to-take" generally means "easy to drink" or "easy to swallow", as the characteristics or property of the solid preparations and the like.

No patent literature discloses or suggests such technical problems.

Means to Solve the Problem

The present inventors have earnestly studied to solve the above problems and completed the invention comprising the following aspects Thus, the present invention provides the following aspects.

[Aspect 1]
A dry-process method for the production of an easy-to-take solid preparation wherein a compression-molded core is coated with a coating agent comprising a gelling agent that will show slipperiness when it is brought into contact with water, comprising directly applying only powder of the coating agent to a mortar inner surface, the bottom end surface of an upper-pestle, and the top end surface of a lower-pestle, and subsequently loading and integrally compression-molding a core-molding material.

[Aspect 2]
The method according to Aspect 1, wherein the gelling agent comprises at least one kind of a water-soluble polymer.

[Aspect 3]
The method according to Aspect 2, wherein the water-soluble polymer is selected from the group consisting of sodium carboxylmethylcellulose, sodium alginate, carrageenan, xanthan gum and gelatin.

[Aspect 4]
The method according to Aspect 3 wherein the water-soluble polymer is sodium carboxylmethylcellulose.

[Aspect 5]
The method according to any one of Aspects 1-4, wherein the coating agent further comprises a lubricant.

[Aspect 6]
The method according to Aspect 5, wherein the lubricant is selected from the group consisting of calcium stearate, magnesium stearate and sucrose fatty acid ester.

[Aspect 7]
An easy-to-take solid preparation that is produced by the method according to Claims 1 to 6.

[Aspect 8]

A powder composition for coating a solid preparation, which comprises sodium carboxylmethylcellulose.

Advantages of Invention

According to the present invention, the easy-to-take solid preparation that is easy to swallow (or, that has an excellent easiness to swallow) can be easily produced by means of a continuous tableting machine conventionally used such as, for example, a simple machine having one injection device, without using any specialized device, means or operation.

Furthermore, since the present invention makes it possible to realize the "easy-to-take" property with the coating processing only by means of mixing and dry compression-molding of the powder so as to produce the easy-to-take solid preparation without going through any wet condition, the functional or active ingredient can be used even if their stability for the solvent is low.

EMBODIMENTS FOR CARRYING OUT THE INVENTION

The present invention relates to a dry-process method for the production of an easy-to-take solid preparation wherein a compression-molded core is coated with a coating agent comprising a gelling agent that will show slipperiness when it is brought into contact with water, comprising directly applying only powder of the coating agent to a mortar inner surface, the bottom end surface of an upper-pestle, and the top end surface of a lower-pestle, and subsequently loading and integrally compression-molding a core-molding material.

Thus, it is not necessary to apply in advance the lubricant to the mortar inner surface, the bottom end surface of the upper-pestle, and the top end surface of the lower-pestle as in the method disclosed PTL 2.

In the method according to the present invention, the mortar, the upper-pestle, and the lower-pestle are a member for compressing the coating agent and the core-molding material along the four directions, so as to mold the easy-to-take solid preparation wherein the compression-molded core is coated with the coating agent. They comprise any other members that are named differently in any other powder compression-molding machines or devices as long as they have substantially the same functions and/or properties as the above ones.

The method according to the present invention does not need such a complicated powder compression-molding machine or device as disclosed in PTL 2, and it can be therefore carried out using such a simple tableting machine as disclosed in the present specification or the continuous tableting machine conventionally used such as, for example, the simple machine having only one injection device.

Each process of applying the powder of the coating agent to the mortar inner surface, the bottom end surface of the upper-pestle, and the top end surface of the lower-pestle; loading or loading the core-molding material, etc. may be performed by any means or method known for those skilled in the art depending on the production machine used and the like. For example, the application of the powder of the coating agent may be carried out by painting or spraying the powder of the coating agent to the mortar inner surface, the bottom end surface of the upper-pestle, and the top end surface of the lower-pestle by using any appropriate means.

The gelling agent that will show slipperiness when it is brought into contact with water according to the present invention means a material that will form a slippery surface of a solid tablet under the moisture condition in the oral cavity when it is taken without water so as to promote the slipperiness of the tablet itself. Such promotion of the slipperiness of the tablet will also make the tablet easy to swallow even when it is taken with water.

The representative examples of the gelling agent include the water-soluble polymer that is selected from the group consisting of sodium carboxylmethylcellulose, sodium alginate, carrageenan, xanthan gum and gelatin. The water-soluble polymer may be naturally-occurring or synthetic one.

The coating agent may comprise the gelling agent only, or further comprise other ingredients as long as they will not inhibit the function of the gelling agent. For example, any material known as a lubricant in the art, for example, those selected from the group consisting of calcium stearate, magnesium stearate and sucrose fatty acid ester may be comprised in the coating agent so as to obtain the advantage that tableting trouble will not likely occur. The ingredients other than the gelling agent may be usually comprised at from 0.01 to 10% by weight of the whole coating agent.

The "powder" in the present invention means the aggregate of solid particulates, which may include powder having finer size or shape than granules or grains. The whole or a part of the surface of the solid preparation may be in the coated condition according to the present invention.

The ingredients comprised in the powder of the coating agent and the core-molding material may be used as they are, or the powder of the coating agent and the core-molding material may be prepared by any means or method known in the art such as a dry granulation process, a wet granulation process and the like.

The dry granulation process includes crushing granulation and roll-compressing method, comprising the steps of compressing each powder components into small bulks with a pressure, and appropriately crushing and granulating them, for example.

On the other hand, the wet granulation process is a method in which each component is dispersed in the presence of water, and the dispersion is dried to form complexes. As specific examples of the wet granulation process, spray methods such as spray drying, tumbling granulation, agitation granulation and fluidized-bed granulation; freeze-drying method; kneading granulation, and the like can be mentioned. They can be produced by any of these methods known to a person skilled in the art.

The easy-to-take solid preparation produced by the method according to the present invention is an oral formulation, and has uses, for example, as various foods such as supplemental foods, nutrition function foods and health foods; and as pharmaceuticals.

The core-molding material in the present invention may therefore optionally comprise various components known for those skilled in the art depending on the above uses.

For use as the foods, for example, it may comprise various nutritional components such as proteins, carbohydrates, lipids and minerals; components for health foods such as various extracts from microorganisms, plants and animals; various vitamins and their derivatives; and designated or existing additives according to Food Sanitation Law, Art. 10; and other components acceptable as a food component (a food additive) listed in a list of general additives for food and drink, such as acidulants, sweeteners, excipients, surfactants, lubricants, auxiliary agents, corrigents, flavoring agents, colorants, and stabilizing agents.

For use as the pharmaceuticals, for example, it may comprise in addition to a medicinal or active ingredient, other any pharmaceutically acceptable components, such as excipients, surfactants, lubricants, auxiliary agents, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia; designated or existing additives according to Food Sanitation Law, Art. 10; natural flavor; and additives listed in a list of general additives for food and drink can be used. There is no limitation in the kind of the medicinal ingredient and the above auxiliaries. Also, the blending ratios of each optional ingredient (component) are not particularly limited as long as the desired effects of the present invention are brought about, and the blending ratios can properly be determined by those skilled in the art.

There is no limitation on an application or kind of the medicinal ingredients, which may include, for example, agents affecting each organ such as the central nervous system, peripheral nervous system, a sensory organ, a circulatory organ, a respiratory organ and a digestive organ and an urogenital organ; hormone drug; agents affecting metabolism such as a vitamin drug, an analeptic, an agent affecting blood and body fluid; agents affecting the function of tissue and cell such as an agent activating cellular function, an agent affecting tumors, an radioactive medicine, an antiallergic agent; medicines based on a medical prescription relating to herbal medicines and Chinese medicines; antibiotics; agents for chemotherapy, biological drug; agents for pathogenic organisms such as parasites; agents for formulation use, diagnosis, public health and in-vitro diagnosis.

The lubricants that may be comprised in the core-molding material can reduce the tableting damage due to the compression molding.

Those skilled in the art may optionally select the various conditions in the processes of the production method according to the present invention, such as pressure and time of the compression-molding, and amounts of the coating agent and the core-molding material, depending on the scale and kind of the machine to be used in the method, the size and application of a desired easy-to-take solid preparation and the like. For example, tablet compression force in the compression-molding usually ranges from 2 to 100 kN.

There is no limitation on the size, shape and the like of the easy-to-take solid preparation according to the present invention. It is usually within a range of from 3 to 20 mm in diameter and of from 15 to 2000 mg in weight, and it may have any shape known for those skilled in the art such as those of a flat with bevel-edge tablet and a truly-flat tablet. The thickness of an outer layer (coating) consisting of the coating agent ranges from about 0.01 to about 0.1 mm. These values can be determined by any method known for those skilled in the art.

The present invention further relates to the easy-to-take solid preparation that is produced by any one of the above methods; and the powder composition for coating the solid preparation, comprising the gelling agent that will show slipperiness when it is brought into contact with water, especially, the water-soluble polymer. A preferable example of the composition is one that comprises sodium carboxylmethylcellulose as the water-soluble polymer.

In addition, contents of all related art documents cited in the present specification are incorporated herein by reference.

Hereinafter, the present invention will more specifically be described with reference to Examples. However, the present invention is not considered to be limited to the Examples.

[Evaluation on Hardness and Slipperiness]

Values of the hardness and slipperiness of the tablets obtained in the Examples and Comparative Example were measured based on the following conditions/methods.

Hardness: Hardness (N) was measured with a digital Kiya hardness tester (Fujiwara Scientific Company Co., Ltd.). The measurement for the hardness was repeated six times for each tablet, and an average value thereof was regarded as a measurement result.

Slipperiness: Three men and women, respectively (six in total) took the tablet without water, and slipperiness was evaluated in accordance with three-stage criteria below:
3: slippery and easy to swallow
2: slightly slippery but hard to swallow
1: hardly slippery and hard to swallow

EXAMPLE 1

18 g of lactose (FlowLac90, MEGGLE JAPAN Co., LTD) and 2 g of hydroxypropylcellulose (HPC-SSL-SFP, NIPPON SODA CO., LTD.) were mixed to give a mixture. The resulting mixture was then subjected to tableting at a tablet compression force of 10 kN with a simple tableting machine (HANDTAB-100, ICHIHASHI-SEIKI Co., Ltd.) to thereby obtain a flat with bevel-edge tablet having a diameter of 8.0 mm and a weight of 250 mg, wherein sodium carboxylmethylcellulose (CMC Daicel, Daicel FineChem Ltd.) had been applied as a coating agent in advance to a mortar inner surface, and the surfaces of an upper-pestle and a lower-pestle in the above tableting machine.

EXAMPLE 2

17.9 g of lactose (FlowLac90, MEGGLE JAPAN Co., LTD), 2 g of hydroxypropylcellulose (HPC-SSL-SFP, NIPPON SODA CO., LTD.) and 0.1 g of calcium stearate (Taihei Chemical Industrial Co. Ltd.) were mixed to give a mixture. The resulting mixture was then subjected to tableting in the same way as in Example 1, except for at a tablet compression force of 12 kN to thereby obtain a flat with bevel-edge tablet having a diameter of 8.0 mm and a weight of 250 mg.

EXAMPLE 3

18 g of lactose (FlowLac90, MEGGLE JAPAN Co., LTD) and 2 g of hydroxypropylcellulose (HPC-SSL-SFP, NIPPON SODA CO., LTD.) were mixed to give a mixture. The resulting mixture was then subjected to tableting in the same way as in Example 1, except that a mixture of 4.975 g of sodium carboxylmethylcellulose (CMC Daicel, Daicel FineChem Ltd.) and 0.025 g of calcium stearate (Taihei Chemical Industrial Co. Ltd.) had been applied as the coating agent in advance to the mortar inner surface, and the surfaces of the upper-pestle and the lower-pestle in the above tableting machine, to thereby obtain a flat with bevel-edge tablet having a diameter of 8.0 mm and a weight of 250 mg.

COMPARATIVE EXAMPLE 1

18 g of lactose (FlowLac90, MEGGLE JAPAN Co., LTD) and 2 g of hydroxypropylcellulose (HPC-SSL-SFP, NIPPON SODA CO., LTD.) were mixed to give a mixture. The resulting mixture was then subjected to tableting in the same way as in Example 1, except that a little amount of calcium stearate (Taihei Chemical Industrial Co. Ltd.) had been applied in advance to the mortar inner surface, and the surfaces of the upper-pestle and the lower-pestle in the above tableting machine and that a tablet compression force was 8 kN, to thereby obtain a flat with bevel-edge tablet having a diameter of 8.0 mm and a weight of 250 mg.

EXAMPLE 4

18 g of lactose (FlowLac90, MEGGLE JAPAN Co., LTD), 1.8 g of hydroxypropylcellulose (HPC-SSL-SFP, NIPPON SODA CO., LTD.) and 0.2 g of calcium stearate (Taihei Chemical Industrial Co. Ltd.) were mixed to give a mixture. The resulting mixture was then subjected to tableting in the same way as in Example 1, except that sodium alginate (KIMICA ALGIN, KIMICA Corporation) had been applied as the coating agent in advance to the mortar inner surface, and the surfaces of the upper-pestle and the lower-pestle in the above tableting machine and that a tablet compression force was 8 kN, to thereby obtain an R6.5 tablet having a diameter of 8.0 mm and a weight of 200 mg.

EXAMPLE 5

18 g of lactose (FlowLac90, MEGGLE JAPAN Co., LTD), 1.8 g of hydroxypropylcellulose (HPC-SSL-SFP, NIPPON SODA CO., LTD.) and 0.2 g of calcium stearate (Taihei Chemical Industrial Co. Ltd.) were mixed to give a mixture. The resulting mixture was then subjected to tableting in the same way as in Example 1, except that xanthan gum (Xanthan gum XG800, Mitsubishi-Chemical Foods Corporation) had been applied as the coating agent in advance to the mortar inner surface, and the surfaces of the upper-pestle and the lower-pestle in the above tableting machine and that a tablet compression force was 8 kN, to thereby obtain an R6.5 tablet having a diameter of 8.0 mm and a weight of 200 mg.

COMPARATIVE EXAMPLE 2

17.9 g of lactose (FlowLac90, MEGGLE JAPAN Co., LTD), 2 g of hydroxypropylcellulose (HPC-SSL-SFP, NIPPON SODA CO., LTD.) and 0.1 g of calcium stearate (Taihei Chemical Industrial Co. Ltd.) were mixed to give a mixture. The resulting mixture was then subjected to tableting in the same way as in Example 1, except for at a tablet compression force of 6 kN to thereby obtain an R6.5 tablet having a diameter of 8.0 mm and a weight of 200 mg.

Tablet Compression Force, Tablet Hardness and Slipperiness of each tablet produced in the above Examples are shown in Table 1.

TABLE 1

|  | Ex. 1 | Ex. 2 | Ex. 3 | Comp. Ex. 1 | Ex. 4 | Ex. 5 | Comp. Ex. 2 |
|---|---|---|---|---|---|---|---|
| Tablet Compression Force (kN) | 10 | 12 | 10 | 8 | 8 | 8 | 6 |
| Tablet Hardness (N) | 100 | 99 | 102 | 82 | 73 | 72 | 109 |
| Slipperiness | 3 | 3 | 3 | 1 | 3 | 3 | 1 |

The results shown in Table 1 demonstrate that the tablets produced in Examples 1 to 5 were more slippery and easy-to-swallow, wherein they were tableted after the water-soluble polymer such as sodium carboxylmethylcellulose, sodium alginate or xanthan gum had been applied to the mortar inner surface, and the surfaces of the upper-pestle and the lower-pestle in the above tableting machine, than those obtained in Comparative Examples 1 and 2 wherein the water-soluble polymer had not been applied. Furthermore, it was not necessary in Examples 1-5 to apply in advance the lubricant to the mortar inner surface, the bottom end surface of the upper-pestle, and the top end surface of the lower-pestle as in the method disclosed PTL 2.

INDUSTRIAL APPLICABILITY

The present invention significantly contributes to research and development of the method for the production of the easy-to-take solid preparation, the easy-to-take solid preparation and the like.

The invention claimed is:

1. A dry-process method for the production of an easy-to-take solid preparation
   comprising:
   directly applying only powder of a coating agent to a mortar inner surface, a bottom end surface of an upper-pestle, and a top end surface of a lower-pestle, and
   loading a core-molding material and integrally compression-molding a core so that the core becomes coated with the coating agent,
   wherein the coating agent comprises at least one water-soluble polymer.

2. The method according to claim 1, wherein the water-soluble polymer is selected from the group consisting of sodium carboxylmethylcellulose, sodium alginate, carrageenan, xanthan gum and gelatin.

3. The method according to claim 2 wherein the water-soluble polymer is sodium carboxylmethylcellulose.

4. The method according to claim 1, wherein the coating agent further comprises a lubricant.

5. The method according to claim 4, wherein the lubricant is selected from the group consisting of calcium stearate, magnesium stearate and sucrose fatty acid ester.

6. The method according to claim 1, wherein the coating agent further comprises a lubricant.

7. The method according to claim 2, wherein the coating agent further comprises a lubricant.

8. The method according to claim 3, wherein the coating agent further comprises a lubricant.

* * * * *